US005155756A

United States Patent [19]
Paré et al.

[11] Patent Number: 5,155,756
[45] Date of Patent: Oct. 13, 1992

[54] METHOD OF CHANGING BETWEEN ANTERO-POSTERIOR EXAMINATION AND LATERAL EXAMINATION WITH AN OSTEODENSIMETER

[75] Inventors: Christian Paré, Plaisir; Guy Bonnet, Wissous; Christophe Fleury, Guyancourt, all of France

[73] Assignee: Sopha Medical, Paris, France

[21] Appl. No.: 709,834

[22] Filed: Jun. 4, 1991

[30] Foreign Application Priority Data

Jun. 6, 1990 [FR] France ............................. 90 06983

[51] Int. Cl.$^5$ ............................................. H05G 1/02
[52] U.S. Cl. .................................... 378/196; 378/193
[58] Field of Search ............... 378/196, 195, 198, 193, 378/209, 208, 189

[56] References Cited

U.S. PATENT DOCUMENTS

| | | | |
|---|---|---|---|
| 3,639,764 | 2/1972 | Olson et al. | 378/193 |
| 4,256,966 | 3/1981 | Heinz | 378/206 |
| 4,653,083 | 3/1987 | Rossi | 378/196 |
| 5,014,292 | 5/1991 | Siczek et al. | 378/196 |
| 5,020,089 | 5/1991 | Cramer et al. | 378/196 |
| 5,068,887 | 11/1991 | Hughes | 378/206 |

FOREIGN PATENT DOCUMENTS

| | | |
|---|---|---|
| 253742 | 7/1987 | European Pat. Off. . |
| 8607531 | 6/1985 | World Int. Prop. O. . |
| 8808688 | 5/1987 | World Int. Prop. O. . |

Primary Examiner—Constantine Hannaher
Assistant Examiner—Don Wong
Attorney, Agent, or Firm—Pollock, VandeSande & Priddy

[57] ABSTRACT

In order to change from antero-posterior examination to lateral examination with an osteodensimeter, the yoke carrying the X-ray tube and the radiation detector of this apparatus is moved laterally. Changeover of the entire assembly is enabled when this lateral translation comes into abutment. When changeover is complete, the return transverse translation is performed. Prior to performing lateral examination, the bed on which the patient to be examined is lying is itself raised. It is shown that this dynamic configuration makes it possible to keep the position of the X-ray tube relative to the detector fixed and as adjusted by construction.

6 Claims, 2 Drawing Sheets

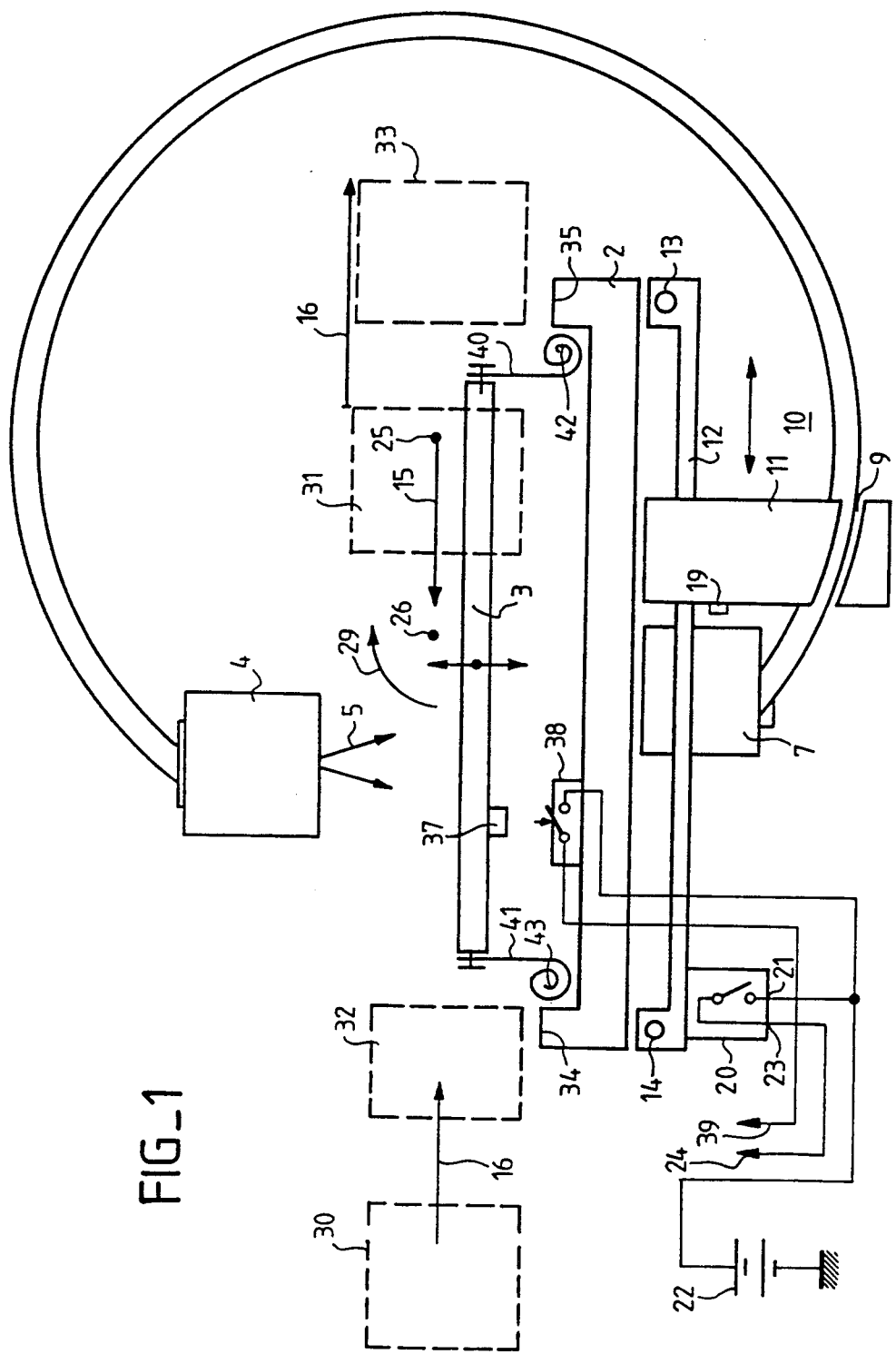
FIG_1

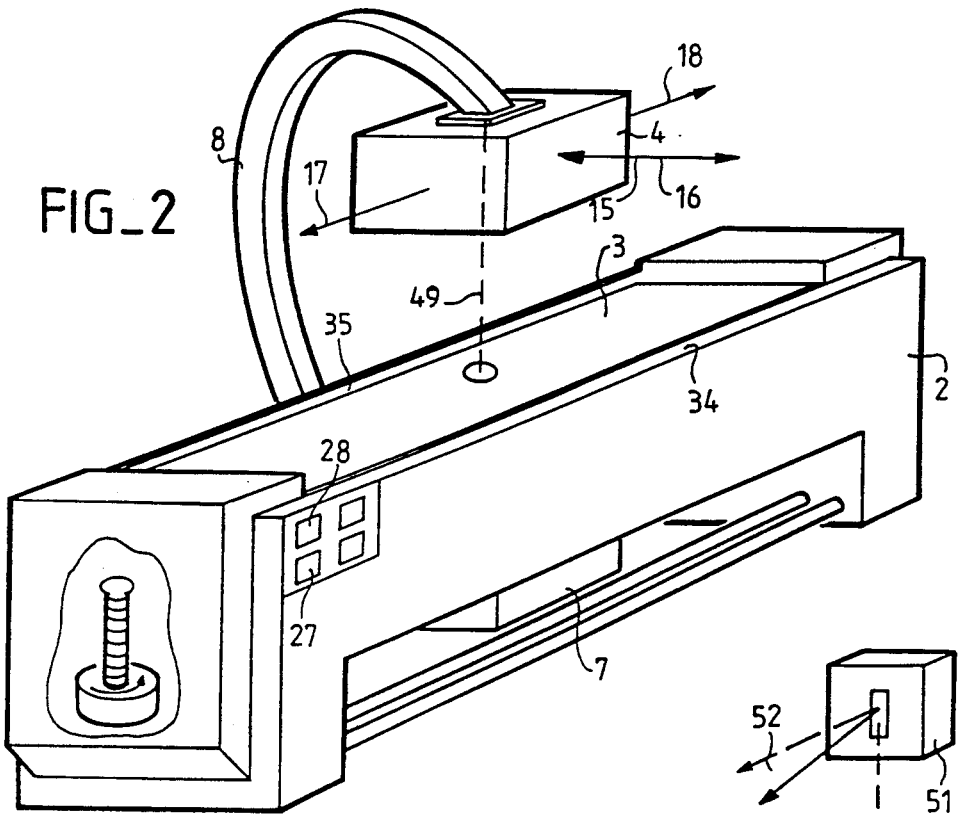
FIG_2
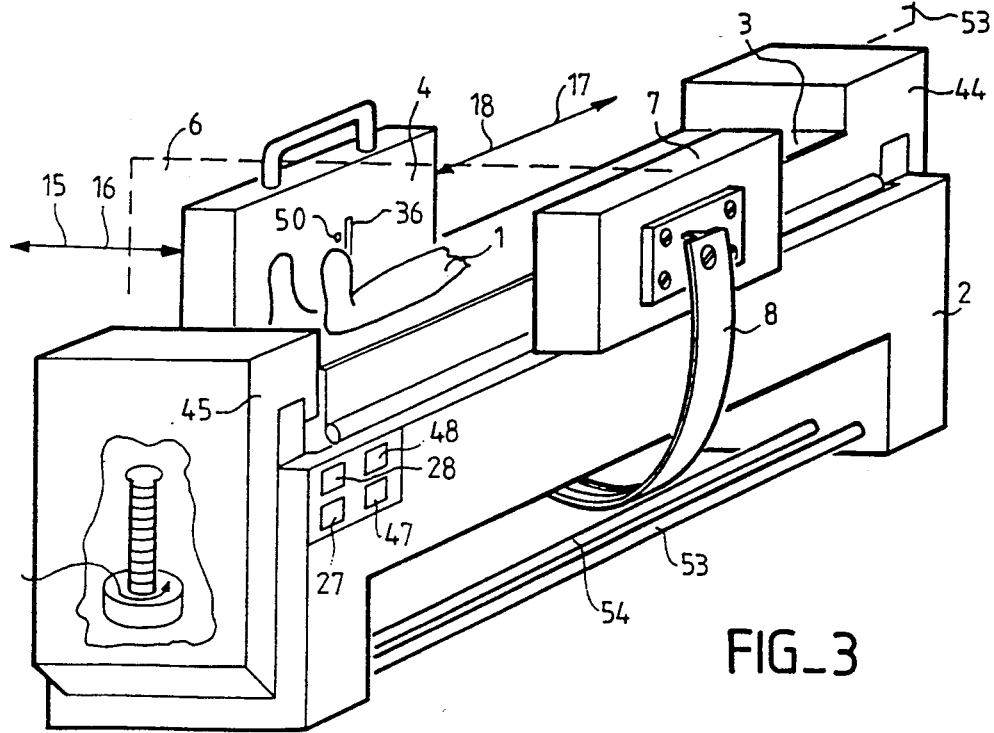
FIG_3

METHOD OF CHANGING BETWEEN ANTERO-POSTERIOR EXAMINATION AND LATERAL EXAMINATION WITH AN OSTEODENSIMETER

The present invention relates to a method of changing from antero-posterior type examination of a patient to lateral type examination, or vice versa, with apparatus for measuring the bone density of parts of the body of the patient.

BACKGROUND OF THE INVENTION

In such an apparatus, a patient lies down on an examination bed, generally on the back. In antero-posterior presentation, an X-ray produced by an X-ray tube passes through the patient downwards and is received by a radiation detector situated beneath the bed. In lateral type examination, X-radiation penetrates the patient on one side and leaves via the other side. Antero-posterior type examination is used to measure the integrity of bones associated with the patient's pelvis: essentially the sacrum and the neck of the femur. Lateral type examination is used to measure the integrity of the spinal column. To keep down costs, installations including such apparatuses need to be capable of performing in both directions. Bone density measurements are used to evaluate bone porosity and thus the strength of bone under stress.

The technique of bone density measurement is known. It consists in irradiating the body of a patient with radiation at given energy; in measuring the attenuation of the radiation; and in repeating the examination with radiation at another given energy. Given the two phenomena whereby the energy of such irradiation is absorbed in the body: Compton absorption; and photoelectric absorption; it is possible to use such measurements to distinguish between different types of tissue depending on their absorption susceptibilities in each of these modes. Radiological absorption by tissue is determined in a space of two dimensions: a Compton effect dimension and a photoelectric effect dimension. Relatively speaking, it is known that bones absorb more in one of these modes while soft tissues absorb more in the other mode. Thus, by changing axis, one of these dimensions can be used to reveal bone density on its own while the other one reveals the amount of soft tissue in the body. To perform such examinations, it is necessary to have an X-ray tube available that emits at two different energies, and also to have a detector capable of distinguishing radiation attenuation at two different energies. In conventional radiology, two tests are performed successively in time, with the emission spectrum of the X-ray tube being changed from one test to the other, and with the bone density measurements being deduced therefrom. The results of these measurements are presented in images.

It is also known that this measurement technique can be combined with the use of gamma cameras. This leads to a simplification of the procedure in that only one test needs to be attempted. So long as a two-channel gamma camera is used, it is capable on its own of counting strikes at one given energy and at another given energy without confusing strike numbers. A gamma camera, also known as an "Anger" camera operates as follows. After passing through the patient, gamma rays are detected by means of scintillation detectors. The incident gamma radiation is transformed into light energy by exciting a scintillator constituted by a thallium-activated sodium iodide crystal (NaI(T1)). The scintillator crystal disposed in this manner on the path of gamma rays after they have passed through the body being examined, serves to transform the gamma rays into light rays. Downstream from the scintillator, the detector further includes a network of photomultiplier tubes. Each photomultiplier tube in the network serves to transform the light energy from the scintillator into electrical pulses. The amplitude of each electrical pulse is proportional to the incident light energy and thus to the energy delivered by the gamma photon to the crystal.

After amplification, electrical pulses are selected from a range of energies by means of an amplitude channel selector. Normally only one range or "amplitude window" is selected in a gamma camera. Nevertheless, the use of two windows is known, in particular with apparatuses specialized in measuring bone density by means of a gamma camera. In other words, a gamma photon passing through the body excites the scintillator crystal, is transformed into a light photon and thereby gives rise to an electrical signal via the network of detection photomultiplier tubes, with the amplitude of the electrical signal being a function of the incident gamma energy. It is thus possible to count such a scintillation as a strike at a specific one of the two energies at the location where it occurs. The location where the scintillation occurs is deduced by processing all of the electrical signals produced simultaneously at the moment of the scintillation by all or some of the photomultiplier tubes in the network, and by calculating the central of gravity thereof. Such processing is generally performed by a computer. After a certain length of time, it is possible to establish the fraction of strikes at one energy and the fraction at the other energy for a given region of the scintillator and consequently for a corresponding region in the body of the patient. Depending on whether the fraction is high or low at the location under consideration, it can be said that the gamma rays that have passed through the body at this location have passed through zones that are boney to a greater or lesser extent. By subsequent image processing, it is then possible to show up the corresponding bone quality., This type of examination is very useful, in particular for showing up troubles with osteoporosis.

To produce radiation at two energies simultaneously, it is possible, for example, to use an X-ray tube which emits a substantially continuous spectrum, e.g. over the range 20 keV to 80 keV, and to feed it with an anode voltage that is at substantially 80 kV relative to the cathode. It would also be possible to use two chemical sources. By then causing the emitted radiation to pass through a neodymium oxide filter ($Nd_2O_3$) having a density of 0.4 grams per square centimeter ($g/cm^2$) before it passes through the body of the patient to be examined, it is possible to obtain a two-photon spectrum having two energy peaks at about 35 keV and about 43 keV. Unfortunately, the filter has the effect of removing 97% of the X-ray photons emitted by the tube. Nevertheless, this is the price that must be paid to go from a continuous spectrum to a two-photon spectrum.

In full-body examination of a patient, it is known that X-radiation can be limited geometrically after filtering to a thin flat fan-shaped beam. During examination, the body of the patient is then displaced perpendicularly relative to the plane of the flat beam so that the beam scans the entire body. Under such circumstances, a network of photomultiplier tubes disposed in a row is placed facing the fan-shaped X-ray beam. The bases of the photomultiplier tubes in alignment with one another then constitute a detection segment. The larger the segment, the greater the number of tubes and the larger the field under examination. This detection segment is minutely adjusted in the plane of the fan-shaped beam at a predetermined distance from the two-photon X-ray source.

Unfortunately, for technological reasons, it is not possible to obtain a very large detection field. In practice, even with an embodiment having 24 photomultiplier tubes in alignment with one another, the resulting field is no more than about 20 cm. In other words, the portion of the body that is examined is the portion of a section of the body lying between the focus of the X-ray tube and the 20 cm detection segment. It will readily be understood that in order to make this section as large as possible, magnification effects should be reduced as much as possible, and so the detector should be placed as close as possible to the body of the patient.

This constraint then means that when the patient is lying on a bed during antero-posterior type examination, the detector, must be pressed against the underside of the bed. Whereas, for a lateral type examination, the detector must be placed as close as possible to the side of the patient being examined.

In an apparatus capable of performing both types of examination, the X-ray tube and the radiation detector are carried at respective ends of a C-shaped yoke.

To pass from one type of examination to the other, the moving C-shaped yoke is caused to slide. Problems of available space are then encountered during sliding. In one known system, provision is made when passing from antero-posterior examination to lateral examination to begin by moving the under-bed detector away from the tube, i.e. the detector is displaced relative to the yoke and in the plane of the yoke. Once this displacement has been performed, the equipment is moved from one incidence to the other by sliding the yoke. Then the detector is returned to its standard position relative to the tube. This technique suffers from the drawback that camera type detectors are very difficult to adjust. In particular, the location processing system for determining where scintillations occur on the detector as a function of the photomultipliers that have detected them is very sensitive to misadjustment or to incorrect resetting of the detector relative to the focus of the X-ray tube. Such a technique is therefore unreliable since images cannot be compared when going from one type of examination to the other on the same patient.

In addition, the two types of examination require the patient to be presented differently on the bed. For an antero-posterior type examination it is necessary to displace the X-ray tube and the detector together horizontally and longitudinally along the patient, or transversely relative to the patient. In contrast, for lateral type examination, the dynamics of the system for changing examination type by sliding is such that the spinal column of the patient (i.e. the part to be examined) now lies well below the alignment of the X-ray tube focus and the detection segment, even if the detection segment is then vertical. One known way of solving this problem is to ask the patient to get off the examination bed so that a thicker mattress can be placed thereon for the purpose of raising the patient's spinal column vertically. In addition to the additional mattress handling, asking the patient to lie down and get up in this way gives rise to time-wasting activity, thereby making the apparatus relatively uneconomic. In a variant, changeover is not complete. Examination is then not completely lateral. The X-ray tube fires diagonally downwards towards the detector. It can be shown that under such circumstances, the examination is not very precise and that in addition because of the shape of the bed, the detector is then at a distance from the patient, thus reducing the effective size of the sector for examination purposes.

An object of the invention is to remedy the drawbacks of prior apparatuses while essentially maintaining the detector in a fixed position relative to the X-ray tube. The detector and the tube are then securely mounted and fixed to opposite ends of a yoke that is capable of sliding.

SUMMARY OF THE INVENTION

Instead of displacing the detector along the yoke when changing the type of examination, the entire yoke is moved in translation. This translation comes into abutment both at one end of the bed (preferably the foot end so as to avoid taking any risks relative to the patient), and laterally in the plane of the yoke. Under these circumstances, already-existing facilities for displacing the apparatus can be used to perform the changeover without it being necessary to use some other displacement facility, and thus displacing the detector on its own, which is detrimental as mentioned above.

More specifically, the invention provides a method of changing over from antero-posterior type examination of a patient to lateral type examination of the patient with apparatus for measuring the bone density of portions of the body of the patient, the apparatus comprising a frame, the frame carrying a bed and a measurement device, the measurement device being provided with an X-ray tube supported on the frame to face a radiation detector by means of a C-shaped changeover yoke which is movable by sliding, the X-ray tube being fixed relative to the radiation detector, the method comprising the following steps:

the measurement device of the apparatus is brought into abutment with a longitudinal end of the bed;

the measurement device is moved in translation relative to the bed and in the plane of the yoke;

changeover is performed by causing the yoke to slide along a slideway fixed to the frame; and the measurement device is again moved in translation in the plane of the yoke, but in the opposite direction, thereby causing it to occupy a position corresponding to the examination to be performed.

BRIEF DESCRIPTION OF THE DRAWINGS

The present invention will be better understood from reading the following description and from examining the accompanying figures. The figures are given purely by way of example and they do not limit the invention. In the figures:

FIG. 1 is a diagrammatic cross-section through apparatus of the invention; and

FIGS. 2 and 3 are perspective views of apparatus of the invention respectively in the antero-posterior position and in the lateral position. FIG. 3 also shows the section plane of FIG. 1.

MORE DETAILED DESCRIPTION

The same references are used throughout the figures which show apparatus for measuring bone density in a portion of the body of a patient 1. The apparatus comprises a frame 2 carrying a bed 3 and a measurement device. The frame 2 is provided with two stiffening spacers 54 and 53. The bed 3 is made of X-ray transparent material. The measuring device comprises an X-ray-generating tube 4 emitting a flat fan-shaped beam of X-rays 5. This flat fan-shaped beam lies in a plane such as the plane 6 (the section plane of FIG. 1 as shown in FIG. 3) perpendicular to the length of the bed 3 on which the patient lies down. A radiation detector 7 is placed facing the X-ray tube 4. The radiation detector 7 is a detector of the type used in gamma cameras. Going from upstream to downstream in the radiation direction, it comprises a scintillator and then an alignment of photomultiplier tubes whose detection bases form a detection segment contained in the plane 6. The detector 7 is also connected to conventional devices (not shown) for signal processing and for displaying images. The X-ray tube 4 and the radiation detector 7 are connected to each other by means of a C-shaped yoke 8. In the example shown, the yoke 8 extends over slightly more than a semicircle such that the tube 4 and the detector 7 are placed on one side of the center of rotation of the yoke while the yoke itself is on the other side.

The C-shaped yoke is capable of sliding in a slideway 9 fixed in moving equipment 10. The moving equipment 10 essentially comprises a base 11 in which the slideway 9 may be hollowed out, for example. The equipment 10 also includes a set of ball bearings (not shown) to enable the base 11 to slide in translation along a cross-bar 12 in a plane which is perpendicular to the long direction of the bed. The cross-bar 12 is shown as having only one rail, but in practice there are two. A first rail is close to the observer of FIG. 1. A second rail is further from said observer. The two rails serve to stabilize the yoke 8. The two rails are offset from the plane 6 in which the detector 7 lies so that it does not encounter them. The cross-bar 12 itself can be moved in translation in the long direction of the bed by sliding along two shafts 13 and 14. The two shafts 13 and 14 are parallel to the bed and each of them is connected at its ends to the frame 2. The bracket 12 allows the measurement device to move in translation in the directions of arrows 15 and 16, while the shafts 13 and 14 allow the moving equipment 10 (and thus the entire measurement device) to move in the directions of arrows 17 and 18 (FIGS. 2 and 3 only).

The method of the invention is as follows. Once the patient is on the bed 3, and it is desired to pass from antero-posterior examination to lateral examination, the measurement device 4, 7, 8 is moved longitudinally to come into abutment against one end of the bed. For example, it is preferable to place it next to the feet of the patient so as to avoid taking any risks of injuring the patient when moving the equipment. In practice, the bed may be long enough to ensure that for most patients the measurement device is moved beyond the feet of the patient. Once this has been done, the measurement device 4, 7, 8 is moved transversely in the direction of arrow 15 by sliding the base 11 along the cross-bar 12. This displacement is continued until a dog 19 fixed to the base 11 closes an end-of-stroke type switch 20 by coming into abutment therewith.

For example, the switch 20 may include two electrical signal terminals, a first terminal 21 connected to a power supply 22 and a second terminal 23 for delivering an enable signal. The enable signal 24 is used in the logic system for controlling displacement of the apparatus to enable rotation of the measurement device.

During this transverse translation motion, the center of rotation of the measurement device 4, 7, 8 is displaced from position 25 to position 26 relative to the bed 3 (FIG. Rotation is motor-driven: the base 11 includes motors (not shown). These motors are actuated by control buttons 27 and 28 that can be seen on the side of the frame 2 (FIGS. 2 and 3). It is preferable for this rotation to be motor-driven since with electrically-powered motors it is possible to take account of the electrical enable signal 24. If the electrical signal 24 is present (positive safety), then the buttons 27 or 28 are active. Otherwise they are inactive.

When the rotation 29 for changing from an antero-posterior position to a lateral position has terminated in this manner, the radiation detector 7 and the X-ray tube 4 lie respectively in positions 30 and 31 shown in FIG. 1. It can be seen that the tube 4 then encroaches somewhat over the bed 3 in its low position 31. The measurement assembly 10 is then moved transversely in the opposite direction in the plane of the yoke 8 and along the cross-bar 12 so as to bring the detector and the tube respectively into positions 32 and 33. In these positions 32 and 33, the detector and the tube both substantially overlie the frame 2 on opposite sides of the bed. However they are then at a very small distance therefrom, leaving a gap of no more than 2 cm.

The frame 2 is thus in the form of a tub receiving the bed 3. The tub has longitudinal rims 34 and 35 over which the detector and the tube can move in translation by sliding the assembly 10 along the shafts 13 and 14.

FIG. 1 shows an additional function of the bed 3 relative to the frame 2: the bed may be raised. In FIG. 2, the bed is shown in its low position. This is the position for performing antero-posterior type examination with the body of the patient then being as close as possible to the detector 7 which is beneath the body. The top of the bed is then flush with the tops of the rims 34 and 35. In contrast, given the position of the spinal column of a patient, FIG. 3 shows the bed raised so that the spinal column of the patient lies substantially in the middle of the field irradiated by the radiation from the tube 4. The irradiated field is a flat field passing through the elongate diaphragm 36 of the tube 4. As shown in FIG. 1, in the preferred embodiment where the bed can be raised, it is necessary for the bed to be in its low position while changeover is taking place so as to leave room for the X-ray tube 4 to occupy location 31. For this purpose, the bed whose movement is controlled from elsewhere includes a dog 37 for closing an end-of-stroke type switch 38 when the bed is in its low position, which switch is also connected to the power supply 22 and serves to deliver an enable signal 39. In practice, and in the preferred variant, rotation under the control of buttons 27 and 28 is enabled only when both of the signals 24 and 39 are active. In order to allow for patients of different sizes, the bed may be capable of being raised by about 20 cm. Thus, in the invention, whenever changing over from one type of examination to the other, the equipment is brought into abutment at the foot of the bed. Transverse displacement is performed, rotation is performed, and transverse displacement is performed in the opposite direction. Finally, the bed is raised. This sequence of operations, which may be automated, replaces the operations of decoupling the detector 7 from the tube 4.

In order to ensure that the hands of the patient are not inadvertently pinched between the bed and the frame 2 when the bed is lowered, the sides of the bed are provided with blinds 40 and 41 that wind resiliently onto respective poles 42 and 43 and whose top ends are riveted to the sides of the bed 3. When the bed is raised, the blinds are paid out, whereas when the bed is lowered they are resiliently wound back onto the poles 42 and 43. In order to enable the bed to be raised, it is carried at its longitudinal ends by brackets 44 and 45 whose vertical portions are suitable for being moved up the frame 2 under drive from motors such as 46 under the control of control buttons 47 or 48 situated close to the buttons 27 and 28.

In prior art type apparatuses, it was known to provide displacement along arrows 15 to 18. However, in the invention, the amplitude of such displacement has been increased so as to make it possible to take the radiation detector 7 clear of the rim 34 of the frame 2, thereby enabling it to be raised to occupy the position 30. Once it in this position 30, the yoke is returned to its position corresponding to 32 and 33. An end-of-stroke type device analogous to those mentioned above serves to prevent the measurement device operating (i.e. serves to prevent measurement being performed) so long as the tube and the detector have not reached positions 32 and 33. Advantageously, they occupy these positions 32 and 33 when the measurement device is maximally displaced to the right (in FIG. 1).

When performing antero-posterior type examination, the position of the measurement device relative to the patient is adjusted by means of a light source, e.g. a laser diode bonded to the X-ray tube and suitable for emitting light radiation 49 whose spot shows the region on the patient that will correspond to the center of the image after image processing. By construction, this spot is aimed on the center of the detector segment. The light ray 49 leaves via an orifice 50 situated close to the radiation diaphragm 36. In contrast, for lateral type examination, a light source 51 is placed on one of the walls of the examination room containing the apparatus. By construction, the light source 51 emits a preferably vertical plane 53 of light radiation 52 which passes longitudinally along the middle of the bed. Given the fixed positions 32 and 33 in which a lateral examination measurement is enabled, the light radiation 52 makes it possible to place the patient in the best possible position on the bed 3. This can be done by the patient squirming or wriggling under instructions given by an operator who can see the line on the patient's body provided by the light radiation 52.

Operations are performed in the opposite order when passing from lateral examination to antero-posterior examination.

We claim:

1. A system for measuring the bone density of a portion of a body of a patient, said system comprising:
    frame means for supporting members in said system;
    a bed member supported by said frame means, said bed member having longitudinally extending sides;
    a measurement assembly supported by said frame means, said measurement assembly comprising a C-shaped yoke disposed in a plane substantially perpendicular to the longitudinally-extending sides of said bed member and an X-ray source and a radiation detector mounted on said yoke so as to face each other;
    slideway means mounted on said frame means for changing said measurement assembly from a position for an antero-posterior radiation examination to a position for a lateral radiation examination, said slideway means movably supporting said measurement assembly for translational movement in a direction parallel to the longitudinally-extending sides of said bed member, and extending to a longitudinal end of said bed member for translational movement in a direction perpendicular to the longitudinally-extending sides of said bed member, and in rotational movement in the plane of said yoke;
    means for moving said measurement assembly on said slideway means in said directions parallel and perpendicular to the longitudinally-extending sides of said bed member and in said rotational movement; and
    means for preventing a changeover of said measurement assembly between antero-posterior position and a lateral position for examination unless said measurement assembly is at said longitudinal end of said bed member.

2. A system according to claim 1 wherein said slideway means comprises:
    a first slideway member mounted on said frame means for movably supporting said measurement assembly for movement in a direction parallel to the longitudinally-extending sides of said bed member; a second slideway member mounted on said first slideway member for movably supporting said measurement assembly for movement in a direction perpendicular to the longitudinally-extending sides of said bed member; and, a third slideway member mounted on said second slideway member for rotatably moving said measurement assembly in the plane of said yoke.

3. A system according to claim 1 wherein means are provided for raising and lowering said bed member relative to said frame means and means are provided for permitting a changeover of said measurement assembly only when said bed member is in a lowered position.

4. A system according to claim 3 wherein roller blinds are provided between said bed member and said frame means to prevent the hands of the patient from being pinched between said bed member and said frame means.

5. A system according to claim 1 wherein said X-ray source is provided with a light source for aiming said X-ray source at said radiation detector.

6. A system according to claim 1 including a light source for indicating the direction of radiation emitted by said X-ray source.

* * * * *

UNITED STATES PATENT AND TRADEMARK OFFICE
CERTIFICATE OF CORRECTION

PATENT NO. : 5,155,756
DATED : October 13, 1992
INVENTOR(S) : Christian Pare, et al.

It is certified that error appears in the above-identified patent and that said Letters Patent is hereby corrected as shown below:

Column 6, line 8, aftre "(FIG." insert --1).--.

Signed and Sealed this

Twenty-first Day of September, 1993

Attest:

BRUCE LEHMAN

Attesting Officer    Commissioner of Patents and Trademarks